(12) United States Patent
Baruth et al.

(10) Patent No.: US 8,724,773 B2
(45) Date of Patent: May 13, 2014

(54) METHOD AND X-RAY SYSTEM FOR PROCESSING AN X-RAY IMAGE

(75) Inventors: Oliver Baruth, Erlangen (DE); Philipp Bernhardt, Forchheim (DE); Richard Obler, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 232 days.

(21) Appl. No.: 13/101,732

(22) Filed: May 5, 2011

(65) Prior Publication Data

US 2011/0274245 A1    Nov. 10, 2011

(30) Foreign Application Priority Data

May 6, 2010 (DE) .......................... 10 2010 019 631

(51) Int. Cl.
*G01N 23/04* (2006.01)
(52) U.S. Cl.
USPC ............................................ 378/52; 382/132
(58) Field of Classification Search
USPC ............... 378/62, 210, 901; 382/128, 132
See application file for complete search history.

(56) References Cited

U.S. PATENT DOCUMENTS 7,315,640 B1 * 1/2008 Brady et al. .................. 382/132
2010/0246918 A1   9/2010 Kappler et al.

OTHER PUBLICATIONS

"Nonlinear Shape Restoration of Distorted Images with Coons Transformation," Lee et al., Proceedings of the Third International Conference on Document Analysis and Recognition (1995), vol. 1, pp. 235-238.
"Restoration of Space-Variant Blurred Image Using a Wavelet Transform," Hashimoto et al., Systems and Computers in Japan, vol. 27, No. 14 (1996), pp. 76-84.
"Restoring Images Degraded by Spatially-Variant Blur," Nagy et al., SIAM Journal on Scientific Computing, vol. 19, Issue 4 (1998), pp. 1-20.

* cited by examiner

*Primary Examiner* — Jurie Yun
(74) *Attorney, Agent, or Firm* — Schiff Hardin LLP

(57) ABSTRACT

To improve the quality of x-ray images, IN a method to process an x-ray image, a mathematical correction of the x-ray image is implemented, wherein the correction at least partially removes from the x-ray image the locally dependent blurring caused by a projection direction-dependent, effective optical focus size of an x-ray tube used to acquire the x-ray image.

11 Claims, 2 Drawing Sheets

METHOD AND X-RAY SYSTEM FOR PROCESSING AN X-RAY IMAGE

BACKGROUND OF THE INVENTION

1. Field of the Invention

The invention concerns a method and system for processing an x-ray image of the type wherein a mathematical correction of the x-ray image is implemented.

2. Description of the Prior Art

In x-ray-based imaging, an x-ray tube with an anode (for example a rotating anode tube) is used as a nearly punctiform x-ray source. In such an x-ray tube, an electron beam in a vacuum housing is accelerated in an electrical field. The electron beam strikes the flat anode made of heavy metal (for example tungsten, molybdenum, rhodium) at a specific angle $\alpha$. The characteristic bremsstrahlung (braking radiation) thereby arises that exits the anode at an angle of 90 degrees and can be used as imaging radiation. The angle $\alpha$ is optimized as a compromise between the following two criteria: the angle should be as large as possible so that a large area can be exposed with it, and the angle should be as small as possible because the smaller the angle, the larger the electrical focal spot size that can be given the same optical focus size, which allows higher pulse power. The angle is generally selected so that it can expose precisely the required area.

The optical focus size is finite and leads to a blurring of x-ray images. Angular anode tubes additionally have the disadvantage that, due to their special geometric arrangement, the optical focus appears compressed or distorted depending on the viewing direction "seen" from the x-ray detector. An illustration of the variation of the focus geometry in different emission directions relative to the central radiation point of the x-ray beam is shown in FIG. 2. This variation—known as focus astigmatism—leads to different, locally dependent blurrings at the x-ray detector or, respectively, the x-ray image.

SUMMARY OF THE INVENTION

An object of the present invention is to provide a method to process an x-ray image which enables an improvement of the quality of an x-ray image. Moreover, an object of the present invention to provide an x-ray system that is suitable for the implementation of such a method.

An image impression in x-ray images that is uniform in all image regions can be achieved by the method according to the invention for processing an x-ray image, wherein a mathematical correction of the x-ray image is implemented, and wherein the correction at least partially removes from the x-ray image a locally dependent blurring due to a projection direction-dependent effective optical focus size of an optical focus of an x-ray tube used to acquire the x-ray image. In addition to a markedly improved and uniform image quality, the danger of misdiagnoses due to unclear image information is thereby decreased. Moreover, an additional processing and handling of the x-ray image is significantly facilitated and therefore also accelerated by the method according to the invention. In particular, after the implementation of the method according to the invention, processing of the x-ray image in spatial frequency space can take place since the x-ray image now no longer exhibits any relevant spatially variant blurring. Viewed mathematically, a spatially variant point spread function is corrected via the method. For example, for this purpose the correction of a spatially variant point spread function can be reduced to the correction of a spatially invariant point spread function, allowing the latter to be processed in a markedly simpler manner. Among other things, this also enables processing by means of the known, very efficient FFT (Fast Fourier Transformation) algorithm.

In an embodiment of the invention, before the correction a projection direction-dependent focus profile of the effective optical focus of the x-ray tube that is used is determined, or retrieved from a memory device. The determination of the focus profile can be implemented, for example, once in the installation or startup of the x-ray system having the x-ray tube (thus for use in a number of x-ray images) or can even be implemented repeatedly for calibration purposes; the determined focus profile can subsequently be stored.

A correction algorithm for mathematical correction of the focus-dependent blurring of the x-ray image can be defined so that the mathematical correction can be implemented via a correction algorithm taking into account the focus profile of the optical focus. This can also be defined from the determined and stored projection direction-dependent focus profile.

According to a further embodiment of the invention, the mathematical correction is fashioned such that a rescanning of the acquired x-ray image is implemented to remove the spatial variance of the focus size of the optical focus.

According to a further embodiment of the invention, the mathematical correction is fashioned such that a correction of the focus-dependent blurring of the x-ray image is implemented using wavelet transformation. Wavelet transformations have the advantage that spatially dependent frequency information can be corrected with them in a simple manner.

A point-by-point calculation of the correction can also be mathematically implemented by solving a large equation system.

For a particularly simple determination of the focus profile of the focus, the optical focus size is advantageously measured in the central beam of the x-ray tube with an aperture plate or a slit. In this way the optical focus sizes outside of the central beam can also be measured. The optical focus sizes outside of the central beam can alternatively also be mathematically calculated from the optical focus size of the focus in the central beam.

According to a further embodiment of the invention, after removing the blurring the x-ray image is subsequently additionally processed in a known manner, in particular by means of a filtering and/or an additional correction. For example, the filtering and/or additional correction can comprise a noise correction and/or a contrast correction and/or a windowing and/or a gamma correction and/or a harmonization and/or an edge accentuation.

To implement the method according to the invention, an x-ray system is provided that has an x-ray tube and an x-ray detector to acquire an x-ray image and a computerized image processing and calculation unit to process the x-ray image. The image processing and calculation unit is configured to implement a mathematical correction of the x-ray image, the correction at least partially removing from the x-ray image the locally dependent blurring caused by a projection direction-dependent, effective optical focus size of the x-ray tube that is used.

The computerized image processing and calculation unit according to the invention for processing acquired x-ray images of an x-ray detector has a program memory to store program code, with a program code that fashioned to implement the method being present in the program memory.

The present invention also encompasses a non-transitory, computer-readable storage medium encoded with programming instructions. When the storage medium is loaded into a computerized processor, the programming instructions cause the computerized processor to implement the method described above, including all embodiments.

DESCRIPTION OF THE PREFERRED EMBODIMENTS

Figure 1:
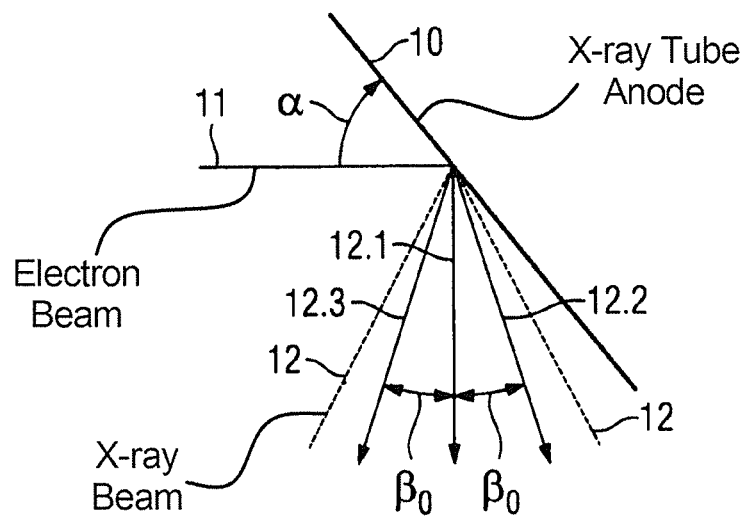
FIG. 1 illustrates the beam geometry of an x-ray tube with anode.
Figure 2:
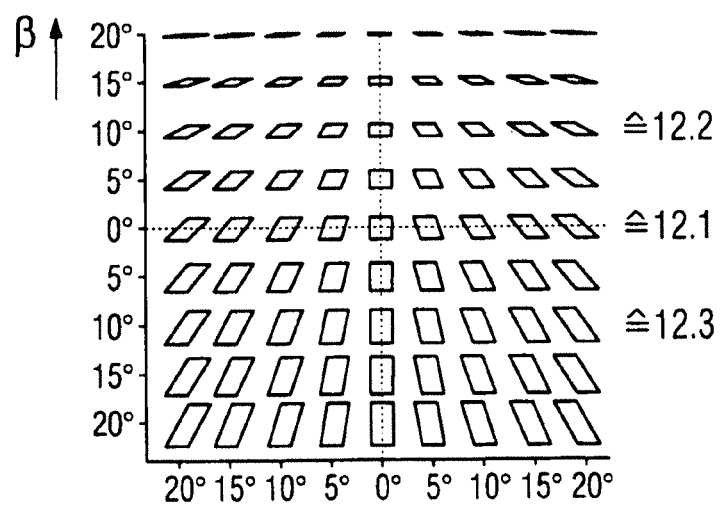
FIG. 2, as noted above, illustrates the variation of the focal spot geometry in different emission directions relative to the central ray of the x-ray beam.

A segment of an anode 10 of an angular anode tube with an electron beam 11 striking the anode 10 at an impact angle α and an x-ray beam 12 with a central ray 12.1 that is thereby generated is shown in FIG. 1. In addition to the central ray 12.1, the x-ray beam 12 is composed of a plurality of rays more or less distant from the central ray. A first edge ray 12.2 that is tilted by an angle β0 relative to the central ray in the vertical emission direction and a second edge ray 12.3 that is tilted by the same angle β0 in the opposite direction are shown as examples. A view of the focus profile—thus the variation of the focus geometry (focus astigmatism) in different emission directions relative to the central beam is shown in FIG. 2, wherein the focus sizes in the directions of the central ray 12.1 and the first side ray 12.2 and the second side ray 12.3 are shown. The focal spot is quadratic in the direction of the central ray; it shrinks to a line towards the anode and enlarges to a rectangle towards the catheter. Since the x-ray beam also varies in the horizontal emission direction, the shown distortions materialize. The quality of the x-ray exposures is thus affected.

The x-ray images are relatively sharp at the anode but here have a lower signal-to-noise ratio since the heel effect somewhat absorbs the dose and the radiation is somewhat harder overall. At the cathode side the x-ray images have a high signal-to-noise ratio since the x-ray radiation can easily leave the anode and a relatively soft x-ray radiation is emitted. However, the images here are very blurry since the optical length of the focus is very large. The optical focus adopts a parallelogram-shaped structure at the corners of the catheter side. A specific direction is therefore extremely blurred.

The originally acquired x-ray image thus has a (generally spatially variant) blurring generated by the focus astigmatism. The method to solve the cited problem according to the invention does so by removal of the (in particular locally dependent) blurring—caused by the focus astigmatism—from the acquired x-ray image. This can on the one hand be implemented mathematically by means of a correction algorithm, or using the measured or determined focus profile. A more uniform impression of sharpness of the x-ray image arises via the correction.

A point-by-point calculation of the correction can be implemented mathematically, for example. However, since the point-by-point calculation can be computationally costly, the complicated problem of what is known as the spatially variant point spread function can also be reduced (viewed mathematically) to the more simply handled problem of a spatially invariant point spread function in order to be able to efficiently calculate with the fast Fourier transformation. Another possibility to reduce the computational cost is to directly account for the spatial variance by means of a wavelet transformation. Efficient algorithms are required today due to the requirement for the latency in real-time applications due to the limited computing capacities. These limitations will presumably no longer be relevant in the future.

The correction algorithm is determined in the background such that it corrects the spatially variant blurring due to the focus profile at least partially, in particular by at least 50% and preferably by at least 80%. Various known solution methods by means of which spatially variant blurring from images can be corrected exist in the prior art. For example, the distortion function and its inverse function can be defined to determine a correction algorithm by means of which the x-ray image can be corrected. In order to remove the blurring, a correction algorithm can then be used for regularized aliasing.

An execution of a suitable transformation to correct the spatial variance of a blurring is known, for example from the article "Nonlinear Shape Restoration of Distorted Images with Coons Transformation", S.-W. Lee, E.-S. Kim, Y. Y. Tang, Proceedings of the Third International Conference on Document Analysis and Recognition, Vol. I, Page 235 and the following, 1995. This article describing the use of a transformation known as a Coons transformation in order to invert the mapping function leading to the spatial variance, wherein contour distortions are incorporated as boundary conditions. According to one embodiment of the invention, after a Coons transformation defined in such a manner a rescanning of the acquired image is obtained and the spatial variance of the focus (thus the point spread function) is compensated.

An additional example is known from "Restoration of Space-Variant Blurred Image Using a Wavelet Transform" von S. Hashimoto, H. Saito, Systems and Computers in Japan, Vol. 27, No. 14, 1996, Pages 76-84. Here wavelet transformations are determined so that a correction of a spatially variant blurring can be calculated efficiently. For the method according to the invention a wavelet transformation can be used correspondingly and be used for a correction of the acquired x-ray image. An additional example for restoration of spatially variant blurring in images is known from "Restoring images degraded by spatially-variant blur" by J. G. Nagy, D. P. O'Leary, SIAM Journal on Scientific Computing, Vol. 19, Issue 4, 1998, Pages 1063 through 1082. Here an image is subdivided into regions with sufficiently spatially variant blur. An efficient aliasing by means of the fast Fourier transformation can be implemented in this way in order to correct the focus-dependent blurring in the x-ray image.

Figure 3:
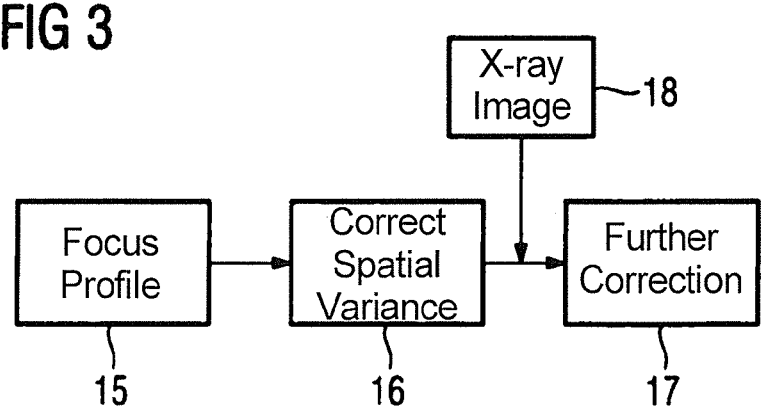
FIG. 3 shows a sequence of an embodiment of a method according to the invention.

Also, for the correction, the focus astigmatism (in addition to the focus profile) can either be detected (by a measurement) or modeled so that the variations of the focus—thus the point spread function—are correctly determined depending on the emission directions. Such an embodiment of the method according to the invention is shown in FIG. 3. In a first Step 15 the focus profile for a specific x-ray tube is determined (for example measured or calculated) once or repeatedly. For example, the focus profile can then be stored. In a second Step 16 the focus profile is used to determine a correction algorithm to correct the spatial variance. In a third Step 17 an x-ray image 18 (for example acquired beforehand by means of the specific x-ray tube) is further corrected by further processing, such as by means of regularized aliasing. A qualitatively improved x-ray image then results from this, which x-ray image can be additionally processed more simply and allows a particularly error-free diagnosis of the acquired examination subject. The determination of the focus profile and of the correction algorithm can take place once (for example) and subsequently be used for all x-ray images generated by the x-ray tube. Image series can also be corrected.

For example, to determine the focus profile the optical focus size (at least in the central ray) can be measured first, for example with the aid of a slit diaphragm or an aperture plate that is set up near the tube. If the slit or the hole is small enough, the focus profile of the central ray is imaged on a detector or image receiver at a significant distance. The focus profile outside of the central ray can subsequently either be measured in a similar manner or be mathematically derived from the central ray measurement. The influence of the aperture plate can additionally be reduced from a measured focus profile (for example via a regularized inverse filtering with the Bessel function) in order to increase the exactness of the focus profile. A two-dimensional Fourier transformation can additionally be implemented for each focus profile. After this was normalized, each Fourier-transformed image can therefore be filtered and a focus correction is obtained given regularized filtering. At least one correction algorithm is determined using the defined or calculated focus profile and focus astigmatism, via which correction algorithm the x-ray image the x-ray image can be corrected in order to remove the (normally spatially variant) blurring.

The x-ray image can subsequently be additionally processed in a conventional manner (in general by means of correction or filtering) in order to optimally adjust noise, edge impression or image contrasts. In particular, additional processing can also be implemented in spatial frequency space, whereby the processing becomes simpler.

Figure 4:
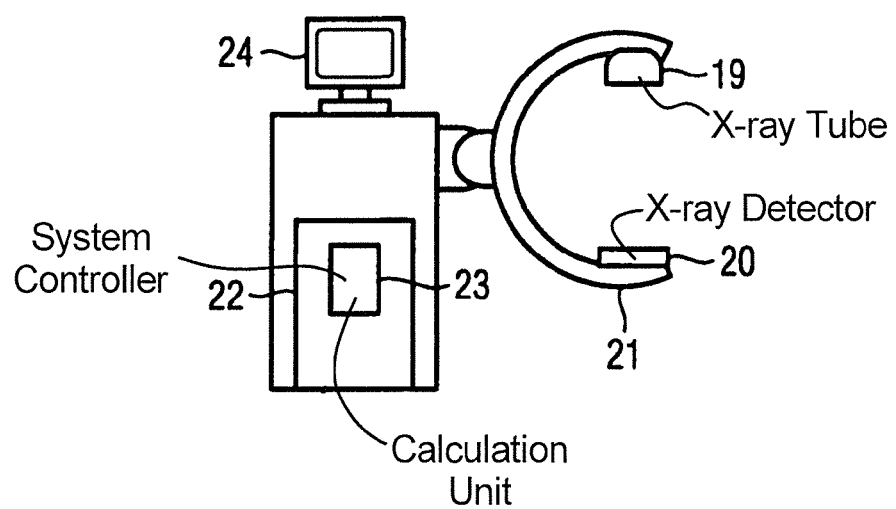
FIG. 4 schematically illustrates an x-ray system according to the invention.

An x-ray system to implement the method according to the invention is shown in FIG. 4. The x-ray system has an x-ray tube 19 and an x-ray detector 20, wherein the x-ray tube 19 has a focus profile as described in FIG. 1 and FIG. 2. The x-ray tube 19 and the x-ray detector 20 can be arranged together on a C-arm 21, for example. The x-ray system has a system controller 22 to activate the complete system as well as an image processing and calculation unit 23 to process the x-ray image. The image proximity and calculation unit 23 is fashioned to determine a transformation for mathematical correction of the x-ray image from the focus profile of the x-ray tube, and to correct the x-ray image by means of the transformation, corresponding to the method of the invention. The system controller 22 can be provided to activate the method, including the determination of the focus profile or its retrieval from a memory device. System controller and image processing and calculation unit can be mutually formed by a computer with a corresponding computer program and program code. The x-ray system can be operated via a user interface at a display 24, at which the corrected image, produced as a datafile, also can be shown.

The invention can be briefly summarized as follows: to improve the quality of x-ray images, a method is provided to process an x-ray image, wherein a mathematical correction of the x-ray image is implemented, wherein the correction at least partially removes from the x-ray image the locally dependent blurring caused by a projection direction-dependent, effective optical focus size of an x-ray tube used to acquire the x-ray image.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for computerized processing of an x-ray image, comprising the steps of:
    supplying electronic data to a computerized processor representing an x-ray image that contains blurring caused by a projection direction-dependent, effective optical focal size of an optical focus of an x-ray tube used to acquire the x-ray image;
    making a projection direction-dependent focus profile of said effective optical focus of said x-ray tube available to said computerized processor; and
    in said computerized processor, automatically implementing a mathematical correction of said x-ray image using said profile to at least partially remove said blurring in said x-ray image in order to produce a corrected image, and making said corrected image available at an output of the processor in electronic form as a data file.

2. A method as claimed in claim 1 comprising determining said focus profile by passing an x-ray beam, having a central ray, through a aperture plate or a slit, and measuring the optical focus size of said focus in said central ray.

3. A method as claimed in claim 2 comprising, in said computerized processor, calculating optical focus sizes outside of said central ray mathematically from said optical focus size of the focus in the central ray.

4. A method as claimed in claim 3 comprising measuring optical focus sizes outside of said central ray.

5. A method as claimed in claim 1 comprising implementing said mathematical correction by executing a correction algorithm in said computerized processor.

6. A method as claimed in claim 1 wherein said data representing said x-ray image comprises a spatial variance of a focus size of the optical focus, and comprising implementing said mathematical correction by rescanning said data representing said x-ray image to remove said spatial variance of the focus size of the optical focus.

7. A method as claimed in claim 1 comprising implementing said mathematical correction by executing a correction algorithm in said computerized processor using wavelet transformation.

8. A method as claimed in claim 1 comprising, after removing said blurring from said x-ray image, further processing the data representing the x-ray image with the blurring removed, by a processing procedure selected from the group consisting of filtering and additional correction.

9. An x-ray system comprising:
    an x-ray tube that emits an x-ray beam from a focus having an optical focus size associated therewith;
    an x-ray detector on which said x-ray beam is incident with a projection of said x-ray beam on said detector, said detector, from said projection of said x-ray beam thereon, generating x-ray image data representing an x-ray image that comprises blurring caused by a projection direction-dependent, effective optical focal size of the optical focus of the x-ray tube; and
    a computerized processor supplied with said x-ray image data and with a projection-dependent focus profile of said effective focus of said x-ray tube, said computerized processor being configured to implement a mathematical correction of said x-ray image data using said profile to at least partially remove said blurring in said x-ray image in order to produce a corrected image, and to make said corrected image available at an output of the processor in electronic form as a data file.

10. An image processor comprising:
    an input supplied with x-ray image data representing an x-ray image comprising blurring caused by a projection direction-dependent effective optical focal size of an optical focus of an x-ray tube used to generate said x-ray image data and supplied with a projection-dependent focus profile of said effective focus of said x-ray tube; and a computerized processor configured to implement a mathematical correction of said x-ray image using said profile to at least partially remove said blurring in said x-ray image in order to produce a corrected image, and to make said corrected image available at an output of the processor in electronic form as a data file.

11. A non-transitory computer-readable storage medium encoded with programming instructions, said programming instructions, when said storage medium is loaded in a computerized processor supplied with x-ray image data representing an x-ray image comprising blurring caused by a projection direction-dependent effective optical focal size of an optical focus of an x-ray tube used to acquire the x-ray image data and with a protection-dependent focus profile of said effective focus of said x-ray tube, causing said computerized processor to:
   implement a mathematical correction of said x-ray image data using said profile to at least partially remove said blurring from said x-ray image to produce a corrected image; and
   make the corrected image available at an output of the processor in electronic form as a data file.

\* \* \* \* \*